United States Patent [19]

McMullen

[11] Patent Number: 4,707,359

[45] Date of Patent: Nov. 17, 1987

[54] INSECTICIDE COMPOSITION FOR CONTROLLING INSECTS WHICH HAVE AN AQUATIC BREEDING SITE

[76] Inventor: Arnold I. McMullen, 70A Quayside Road, Bitterne Manor, Southampton, Hampshire SO2 4AD, England

[21] Appl. No.: 760,728

[22] PCT Filed: Nov. 20, 1984

[86] PCT No.: PCT/GB84/00397

§ 371 Date: Jul. 17, 1985

§ 102(e) Date: Jul. 17, 1985

[87] PCT Pub. No.: WO85/02093

PCT Pub. Date: May 23, 1985

[30] Foreign Application Priority Data

Nov. 21, 1983 [GB] United Kingdom ............... 8331010
May 22, 1984 [GB] United Kingdom ............... 8413024

[51] Int. Cl.$^4$ ...................... A61K 39/07; A01N 63/00
[52] U.S. Cl. ........................................ 424/92; 424/93; 435/822; 435/832; 71/3
[58] Field of Search .................... 424/92, 93; 435/823, 435/832; 71/3

[56] References Cited

U.S. PATENT DOCUMENTS

| | | | |
|---|---|---|---|
| 4,160,033 | 7/1979 | Garrett et al. ........................ 424/283 |
| 4,166,112 | 8/1979 | Goldberg .............................. 424/93 |
| 4,187,290 | 2/1982 | Goldberg .............................. 424/93 |
| 4,325,937 | 4/1982 | Spencer ................................ 424/88 |
| 4,609,550 | 9/1986 | Fitz-James ........................... 424/93 |

FOREIGN PATENT DOCUMENTS

| | | |
|---|---|---|
| 2436565 | 4/1980 | France . |
| 7923342 | 4/1980 | France . |
| 2032277 | 8/1980 | United Kingdom . |
| 2108845 | 5/1983 | United Kingdom . |

OTHER PUBLICATIONS

Paper by Cline et al., "Journal of Economic Entomology", vol. 66, No. 3, Jun. 15, 1973, pp. 697-702.
Cline et al., "Larvicidal Activities . . . Water Dispersions" J. Economic Entomology, vol. 66(3) 1973, pp. 697-702.

Primary Examiner—John Kight
Assistant Examiner—Garnette D. Draper
Attorney, Agent, or Firm—Schweitzer & Cornman

[57] ABSTRACT

An insecticide composition for controlling the breeding of insects (particularly mosquitos) which have aquatic breeding sites comprises two components, the first being either an insoluble monomolecular layer, an insoluble foam layer or a duplex film layer and the second having a toxic action on larvae, the combination of the two components providing a synergistic mixture.

9 Claims, No Drawings

INSECTICIDE COMPOSITION FOR CONTROLLING INSECTS WHICH HAVE AN AQUATIC BREEDING SITE

This invention relates to insecticide compositions for controlling the breeding of insects which have aquatic breeding sites.

In the specification of our British Pat. Nos. 1 357 952 (March 1971) and 1 557 804 (October 1976) there is disclosed a method of controlling the breeding of mosquitoes by forming an insoluble monomolecular layer on the surface of water to reduce the number of mosquito pupae and larvae.

The monomolecular layer is particularly effective in killing the mosquito at certain stages of the life cycle, namely the ovipositing female, fourth stage larva, pupa and emerging adult. It is lethal because the decrease in surface tension causes wetting of the respiratory trumpets of the pupae and larvae and also forms a physical barrier to surface penetration, thus preventing oxygen uptake from the atmosphere by the larvae and pupae. The application of monolayers to the control of mosquito juveniles is described in:

1. McMullen, A. I. & Hill, M. N., (1971), Nature, 234, No. 5323 pp 51–52.
2. McMullen, A. I., Reiter, P. & Phillips, M. C., (1977), Nature, 267, No. 5608 pp 244–245.
3. Garrett, W. D., (1976), Naval Res. Lab. Report 8020, p 13, Washington D.C.

In the specification of our British Pat. No. 1 561 088 there is disclosed a method of controlling the breeding of insects which have an aquatic phase in their life cycle by forming an insoluble foam layer on the surface of the water. This foam layer presents an impenetrable barrier to pupae and larvae of the insects, again wetting their respiratory system and preventing oxygen uptake.

The foam method is more effective than the monomolecular method in that it is effective in killing the mosquito at all stages in its life cycle, namely: ovipositing female, egg, first, second, third and fourth stage larva, pupa and emerging adult. It is, however, more expensive than the monomolecular method in both dosage and application equipment.

There are also specific toxins obtained from *Bacillus thuringiensis* cultures (hereinafter referred to as B.t.) and from *Bacillus sphaericus* cultures which are mainly effective against first, second and third stage mosquito larvae but suffer from the disadvantage that the toxin crystal is dense and rapidly sinks below the feeding zones of young larvae. It is also rapidly inactivated by particulate matter in the catchment.

It has unexpectedly been found that by mixing the toxin from *Bacillus thuringiensis* or *Bacillus sphaericus* with the material forming the monomolecular layer, the toxin is retained at the surface for quite long periods and is transported or spread over wide areas. When the toxin is mixed with an insoluble foam layer the toxin is held at the surface for periods depending on the speed of breakdown of the foam, which depends on the amount applied and the extent of water pollution. Alternatively, the monomolecular layer and toxin mixture can be applied to the water surface with a thin oil layer applied on top thereof, thus forming a "duplex film". These methods of applying the toxin to a water catchment result in a much more effective method for killing mosquitoes than by applying the monolayer, foam, thin oil or the toxin alone. Thus the combination produces a synergistic mixed product.

According to the present invention there is provided an insecticide composition for controlling insects which have an aquatic breeding site comprising a first component which is capable of forming either a monomolecular layer, an insoluble foam layer or a duplex film layer on the surface of a water catchment and a second component which has a toxin action (preferably rapid) on larvae, giving rise to a synergistic mixture.

The first component may be any one or more of the compounds referred to in the specification of British Pat. Nos. 1 557 804 and 1 561 088. Thus the first component may include at least one long chain compound of the general formula:

$$C_mH_{2m\pm1}.(OR)_nOH$$

or $$C_mH_{2m\pm1}.(OR.OB)_nOH$$

and/or at least one long chain compound of the general formula:

$$C_mH_{2m\pm1}.CO.(OR)_nOH$$

or $$C_mH_{2m\pm1}.CO.(OR.OB)_nOH$$

where these include branched chain isomers, e.g.:

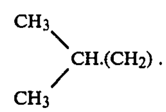

. . . etc., but excepting isostearyl alcohol or acid (see p. 13–14).

In these formulae R and B are alkylenes and may be the same or different, n is an integer in the range 1 to 3 and m is an integer greater than 14.

Such a compound is capable of forming an insoluble monomolecular layer, a foam layer or, (in the presence of an oil), a duplex film, on the surface of a water catchment.

Preferably, the first component comprises a mixture of cetyl, stearyl and oleyl mono- or di-ethoxylates.

The second component may be any specific mosquito larval toxin such as that obtained during growth of bacterial cultures, for example, that toxin found in *B. thuringiensis* H-14 (Bt-H14) or in *B. sphaericus* preparations, the toxin being a high molecular weight protein which splits into active sub-units inside the larvae.

The toxin from Bt-H14 can readily be produced by deep-liquid fermentation using for example the method described by Nickerson, K. W. and Bulla, L. A., *App. Microbiol.*, (1974), 28, pp 124–128.

This produces an aqueous dispersion whose toxin content depends on a number of variables. However, an arbitrary and comparative standard, assessed by bioassay, of about 1000 International Units per mg. is aimed for.

Methods for obtaining compounds suitable for the first component are described in British Patent Specification Nos. 1 557 804 and 1 561 088.

The components of the insecticide composition may be formulated for application to water in several ways.

(1) Monomolecular Layer Formulation (A) Where the first component is in the form of a hydrophobic soft wax or "oil" at ambient temperatures and the second component is in a dehydrated, spray-dried or freeze-dried solid form (produced from the aqueous dispersion obtained from fermentation as described above) the two components are mixed in the desired preparations as 100% "active ingredients" and applied directly to the water surface.

(B) When the first component may be solid or semi-solid, it may be prepared by gradually adding it to water being stirred vigorously in a high speed mixer, emulsifier or colloid mill to form a dispersion having a concentration of from 10% to 20% w/v. This preparation may be mixed directly with a dispersion in water of the second component, the two being mixed to the required content of each ingredient.

(C) Where the first component is in the form of a dispersion as described in (B) above, and the second component is in a solid form as described in (A) above, the solid second component is immersed and mixed within the aqueous dispersion of the first component for a period of several hours before application to the water surface. In each and every case the mixtures must be well shaken to distribute the Bt-H14 toxin in suspension, just prior to application.

(2) Duplex Film Formulation

Compared with the monomolecular layer formulation this has an additional oil component as a major proportion of the content (90%–99%).

(3) Foam Formulation

This may be produced most easily from monomolecular layer formulation (B) described above (but diluted with water to 1% a.i.) by the injection of air or other gases using foaming equipment as described in British Pat. No. 1 561 088 or as mentioned on p. 7.

The insecticide composition may include an extender such as water or an oil, for example a vegetable oil such as soya bean oil or coconut oil or a light mineral oil such as diesel oil, petrol oil, dieseline, etc.

The following table provides examples of the various formulations prepared as described above, giving the preferred concentration ranges for each ingredient.

near the surface, giving excellent control of mosquito juveniles.

The foam forming material may be foamed in several ways. One method is to generate a gas (e.g. carbon dioxide) chemically within an aqueous suspension (1% a.i.) of a foam forming material. A second method is to bubble air or gas from a separate source, for example, a pump, a generator or a pressure cylinder (e.g. a commercial fire extinguisher) through an aqueous suspension of foam forming material. A third method is to inject high pressure air or gas through fine holes into a branch pipe simultaneously with an aqueous suspension of the foam forming material, the relative volumes of air or gas and foam forming material being adjusted to provide the desired texture of the foam layer. In yet another method the insecticide composition is expressed under pressure through a special foam forming nozzle which entrains air into the composition thereby producing a stable water-insoluble foam.

It is preferable that the foam layer formed is at least 0.1 cm in thickness. The foam may be applied at a rate of 1.0 to 5.0 g of active ingredient per square meter which forms a foam layer about 0.1 to 0.5 cm in thickness and which may reduce to a single bubble layer eventually, which is, nevertheless, still effective.

When the surface of the water catchment is moving, the surface must be made static by employing a physical barrier, e.g. by means of a buoyant boom tethered or anchored around the appropriate area. Suitable physical barriers are described in British Patent Specification No. 1 561 088.

Ideally an insecticide composition contains no unspecific toxin or pollutive materials, and the materials used are biodegradable.

The following examples illustrate the improved killing properties of insecticide compositions according to the invention compared with the toxin from *B. thuringiensis* var. H14 alone.

(A) EXAMPLE OF ENHANCED FLOTATION OF TOXIN BY MONOLAYER

The comparison is made between (a) Bt-H14 preparation alone and (b) Bt-H14+"Monoxci" monomolecular

| SURFACE-ACTIVE FORMULATIONS OF MONOLAYER, DUPLEX FILM AND FOAM MIXES WITH TOXIN | | | | | |
|---|---|---|---|---|---|
| TEXT NO. | FORMAT | FIRST COMPONENT 1. | SECOND COMPONENT 2. | EXTENDERS-FILLERS OIL$_3$. WATER$_4$. | APPROX. RATIOS (w/w) 1:2:3:4 |
| (1) (A) | Monolayer | 100% (liquid) | Approx. 1000 IU/mg Dehydrated | None | 0.1:0.9:0:0 to 0.9:0.1:0:0 |
| (B) | Monolayer | 15% (approx) aqueous suspens$^n$ | Approx. 1000 IU/mg Aqueous suspens$^n$ | None | 0.1:0.9:0:0 to 0.9:0.1:0:0 |
| (C) | Monolayer | 15% (approx) aqueous suspens$^n$ | Approx. 1000 IU/mg Dehydrated | None | 0.1:0.9:0:0 to 0.9:0.1:0:0 |
| | Duplex film | 100% (liquid) | Approx. 1000 IU/mg Dehydrated | Oil | 0.1:0.9:99 to 0.9:0.1 0.5:4.5:95:0 4.5:0.5 |
| (3) | Foam | 15% (approx.) aqueous suspens$^n$ | Approx. 1000 IU/mg aqueous suspens$^n$ | Water | 0.1:0.9:0.99 to 0.9:0.1 0.5:4.5:0:95 4.5:0.5 |

The insecticide composition once formulated may be applied to the water catchment to form a monomolecular layer, as a self-spreading suspension of "slurry" by means of droppers, drip-feed reservoirs, spray equipment or by sorbent and inert materials which have been soaked in the concentrated mixture and which float on the surface of the water. The toxin component is thereby spread and maintained in an active state on or layer (Monoxci is a mixture in water of cetyl, stearyl and oleyl alcohol monoethoxylates in a ratio of about 25:25:50 or 15:35:50 as described in British Pat. No. 1 557 804) added to the same area of surface in identical separating funnels (A & B) with bottom outlets for withdrawing aliquots at various time intervals.

Procedure (i) Place 100 ml distilled water in each of A and B,
(ii) Place 100 μl of preparation (a) on surface of water in A and 100 μl of (b) on surface in B.
(iii) Draw off 8 ml of liquid from each of A and B at various time intervals t1, t2, t3, . . . etc.
(iv) Place these aliquots on the surface of 200 ml of water in series of bowls A't1, A't2, . . . B't1, B't2 . . . etc., each containing 25 third instar larvae of *Ae-aegypti.*
(v) Determine larval mortality in each bowl after 24 hours.

Results

TABLE 1

| Time | Mortality (%) | |
|---|---|---|
| (t) hours | (a) series | (b) series |
| 2 | 92 | 0 |
| 3 | 88 | 0 |
| 18 | 72 | 4 |
| 20 | 68 | 20 |
| 22 | 64 | 40 |
| 24 | 40 | 44 |
| Remainder: | 60 | 100 |

Conclusions

The presence of Monoxci monomolecular layer has a positive flotation effect on the dense Bt-H14 particles such that no significant amounts of the latter sediment from the surface during the first 18 hours. In the absence of monomolecular layer the Bt-H14 particles sediment rapidly at the outset (91% larval kill within 2 hours) thus when used in the field this material would be largely inaccessible to the feeding larvae.

(B) EXAMPLES OF SURFACE SPREADING OF TOXIN BY MONOLAYERS (1) The comparison is made between (a) Bt-H14 preparation alone and (b) Bt-H14+Monoxci monomolecular layer added to the first section (A) of a 2 meter long trough which is divided into 4×50 cm sections (A, B, C, D) each containing 3 liters distilled water.

Procedure

Place 0.6 ml aliquots of this mixture or sample to be investigated, on the surface at the extreme end of the trough, in Section A. After two minutes place dividers between sections to confine the larvae. Add 10 mosquito larvae to each section. Record mortalities after 24 hours.

Results

TABLE II

| | % Mortalities | | | |
|---|---|---|---|---|
| Section | A | B | C | D |
| Bt-H14 alone | 100 | 0 | 0 | 0 |
| Bt-H14 + Monoxci | 100 | 100 | 100 | 100 |

Conclusions

Bt-H14 toxin is carried by the spreading monomolecular layer over water catchment surfaces for a distance of at least 2 meters from the source of application and, judging from the period of time the monomolecular layer retains the Bt-H14, shown in experiment (A) above, the Bt-H14 may be carried for the full distance covered by the monomolecular layer. This is normally to the full extent of the available water surface, provided sufficient monomolecular layer is present to cover that surface completely.

(2) Using 100% (non-aqueous) monolayer and Bt-H14 mixtures, similar experiments to the above but including a final 'overflow' test were carried out where 2 liters of water are passed through the end of the trough during a 12-hour period, draining the excess monolayer+Bt-H14 out of the system, into a container (E) where the overflow is bioassayed as in the other sections, when the process is completed.

These experiments were carried out to determine the difference in spreading effectiveness of the following monolayer compositions, under the same conditions and concentrations; namely 10 ul of a 1% mixture of Bt-H14 in the monolayer concentrate.

(i) 90% oleyl alcohol monoethoxylate + 10% cetyl/stearyl diethoxylate,
(ii) 90% oleic acid monoethoxylate + 10% cetyl/stearyl diethoxylate.

Results
Representative examples are:

TABLE III

| Monolayer (i) - alcohol ethoxylate (*Ae. aegypti*, 24 hrs.) | | | | | | |
|---|---|---|---|---|---|---|
| Section | A | B | C | D | E | TOTAL |
| Live larvae | 0 | 0 | 0 | 2 | 6 | 8 |
| Dead Larvae | 10 | 10 | 10 | 8 | 34 | 72 |

TABLE IV

| Monolayer (ii) - acid ethoxylate (*Ae. aegypti*, 18 hrs.) | | | | | | |
|---|---|---|---|---|---|---|
| Section | A | B | C | D | E | TOTAL |
| Live larvae | 0 | 0 | 4 | 8 | 5 | 17 |
| Dead larvae | 10 | 10 | 6 | 2 | 35 | 63 |

Conclusions

Both acid and alcohol ethoxylated monolayers impart very good spreading properties to the toxin particles resulting in a synergistic action on mosquito juvenile control.

Comparison with AROSURF

This material purports to be isostearyl diethoxylate and has been used in a mixture with Bt-H14 and *B. sphaericus* (see Levy, R. E. & Garrett, W. D. et. al., (November 1982), J. Florida Anti-Mosquito Assn., 53, No. 2). It is claimed to have insoluble monolayer properties and an "accelerated spreading potential" of the Bt-H14 is also suggested.

The following two experiments demonstrate that AROSURF is neither insoluble nor synergistic whilst the compositions disclosed in this application and in accordance with the invention are both insoluble and synergistic.

(i) Spreading Tests

The bioassay 'flow' tests described above in B(2) were carried out also with AROSURF with the following results:

TABLE V

| Monolayer - isostearyl diethoxylate (AROSURF) (*An. stephensi*, 24 hrs.) | | | | | | |
|---|---|---|---|---|---|---|
| Section | A | B | C | D | E | TOTAL |
| Live larvae | 8 | 9 | 10 | 10 | 33 | 70 |
| Dead larvae | 2 | 1 | 0 | 0 | 7 | 10 |

Conclusions

When the AROSURF is compared with those monolayers disclosed in this application it is seen that the AROSURF is an inefficient carrier for the Bt-H14 toxin and therefore does not give a synergistic mixture with it:

| Monolayer | Total % Mortality |
|---|---|
| ex Table III | 90 |
| ex Table IV | 79 |
| ex Table V | 13 |

(ii) Solubility Test

The monolayer under test is applied to the surface of water in a vessel (A) which is sealed at the bottom by a dialysis membrane which permits only the passage of molecular species (with a molecular weight below about 20,000 Daltons). This vessel is then placed within a second vessel (B) containing water so that both water surfaces equilibrate to the same level. A surface balance probe, which measures the presence of adsorbed monolayrs, is inserted into the surface of the water in (B). Measurements of the adsorbed monolayer surface pressure (clean water surface pressure=0 dyne/cm) are made after various time intervals.

Results

TABLE 6

| Time (hrs) | Surface pressure (dyne/cm) at: | | | | | |
|---|---|---|---|---|---|---|
| | 1/4 | 1/2 | 1.0 | 2.0 | 16.0 | 20.0 |
| Monolayers described in this application | 0 | 0 | 0 | 0 | 0 | 0 |
| AROSURF | 7 | 11 | 15 | 18 | 20 | 30 |

It is clear that major surface-active molecular or micellar components from the AROSURF preparation pass into the water and through the dialysis membrane to readsorb at the surface of water phase 'B'. On the other hand the monolayers disclosed in this application are substantially insoluble in water. Similar results are obtained when the dialysis membrane is replaced by a 0.45 mm nylon mesh.

Conclusions

The presence of water-soluble components in AROSURF is also shown by its property of spontaneous emulsification whereby the components are immediately distributed within the aqueous phase when AROSURF is applied to water surfaces. The effect of this would be to transfer the Bt-H14 toxin, when mixed with it into the aqueous phase rather than to retain the toxin at the surface. It is therefore submitted that the publication by Levy, R. E. & Garrett, W. D. et. al., (November 1982), J. Florida Anti-Mosquito Assn., 53, No. 2, does not consitute prior art disclosure of the invention claimed herein.

(C) STATIC TESTS

These tests of Monoxci-Bt-H14 mixtures against *C. fatigans* larvae were carried out by Dr. S. H. Ho of Singapore University.

(Monoxci: 15% a.i. aqueous dispersion)

Monoxci and Bti were mixed in the ratio of 6:1 (w/w). Different dosages were tested against various juvenile stages.

(1) Larvae 20 egg rafts were put into each fibre glass tank containing 60 liters of water (area of water surface=6528 sq. cm). The larvae were allowed to hatch and grow to the appropriate stages for the experiments. The chemical mixtures were spread on the water surface. Six samples were taken from each tank after 48 hours. For each sample the numbers of live and dead insects were recorded (Table VII).

TABLE VII

Effect of Monoxci-Bti mixtures on the mortality of larvae of *C. fatigans*.

| Stage | g. of Monoxci-Bti mixture | No. of larvae (48 h) | | 48 h % mortality |
|---|---|---|---|---|
| | | Alive | Dead | |
| 2nd larvae | 0 | 77 | 0 | 0 |
| | 0.06 | 2 | 144 | 98.6 |
| | 0.3 | 0 | 145 | 100 |
| | 0.6 | 0 | 71 | 100 |
| 4th larvae | 0 | 53 | 0 | 0 |
| | 0.06 | 1 | 54 | 98.2 |
| | 0.3 | 1 | 53 | 98.1 |
| | 0.6 | 0 | 44 | 100 |

(2) Egg Hatch 3 replicates of 1 egg raft per plastic tank were set up. The number of larvae that hatched from each raft and mortality of the first instar larvae were recorded (Table VIII).

NOTE: The results obtained from the 3 replicates of each treatment in all experiments were pooled.

TABLE VIII

Effect of Monoxci-Bti mixtures on the hatching of eggs.

| g. of Monoxci-Bti mixture | No. of eggs that hatched (1 day) | % of dead larvae (4 days) |
|---|---|---|
| 0 | 319 | 0 |
| 0.003 | 325 | 100 |
| 0.015 | 282 | 100 |
| 0.03 | 292 | 100 |

Conclusions

The monolayer/Bti mixture is a very effective *C. fatigans* larvicide.

We claim:

1. An insecticide composition for controlling insects which have an aquatic breeding site, comprising an effective insecticidal amount of a first component which when applied to the surface of a water catchment forms an insoluble monomolecular layer or an insoluble foam layer effective in killing insects at certain stages in their life cycle, said first component being selected from the group consisting of $C_mH_{2m+1}.(OR)_nOH$, $C_mH_{2m-1}.(OR)_nOH$, $C_mH_{2m+1}.(OR.OB)_nOH$, $C_mH_{2m-1}.(OR.OB)_nOH$, $C_mH_{2m+1}.CO.(OR)_nOH$, $C_mH_{2m-1}.CO.(OR)_nOH$, $C_mH_{2m+1}.CO.(OR.OB)_nOH$, $C_mH_{2m-1}.CO.(OR.OB)_nOH$, where R and B are alkylenes and may be the same or different, n is an integer in the range 1 to 3 and m is an integer greater than 14, said group being exclusive of isostearyl ethoxylates; and an effective larvacidal amount of a second component comprising a mosquito larva toxin obtained during growth of bacterial cultures, the first and second components giving rise to a synergistic mixture having a greater effectiveness in control of insects than that exhibited by either the first or second component alone.

2. A composition according to claim 1 wherein said toxin is derived from a bacillus selected from the group consisting of *Bacillus thuringiensis* and *Bacillus sphaericus*.

3. A composition as claimed in claim 1 wherein the first component forms an insoluble monomolecular layer and the second component is a toxin derived from *Bacillus thuringiensis* or *Bacillus sphaericus*.

4. A composition as claimed in claim 1 wherein the first component forms an insoluble foam layer and the second component is a toxin derived from *Bacillus thuringiensis* or *Bacillus sphaericus*.

5. A composition as claimed in claim 3 wherein said first component forms an insoluble monomolecular layer that is provided with a thin layer of oil on top of said insoluble monomolecular layer thereby forming a duplex film.

6. A composition as claimed in claim 1 wherein said first component comprises a mixture of cetyl, stearyl and oleyl mono- or di-ethoxylates.

7. A method of controlling the breeding of insects which have an aquatic phase in their life cycle, comprising applying to a water catchment an insecticide composition comprising an effective insecticidal amount of a first component which forms an insoluble monomolecular layer or an insoluble foam layer on the surface of the water, each of which layers effectively kills insects at certain stages in their life cycle, said first component being selected from the group consisting of $C_mH_{2m+1}.(OR)_nOH,$ $C_mH_{2m-1}.(OR)_nOH,$ $C_mH_{2m+1}.(OR.OB)_nOH,$ $C_mH_{2m-1}.(OR.OB)_nOH,$ $C_mH_{2m+1}.CO.(OR)_nOH,$ $C_mH_{2m-1}.CO.(OR)_nOH,$ $C_mH_{2m+1}.CO.(OR.OB)_nOH,$ $C_mH_{2m-1}.CO.(OR.OB)_nOH,$ where R and B are alkylenes and may be the same or different, n is an integer in the range 1 to 3 and m is an integer greater than 14, said group being exclusive of isostearyl ethoxylates; and adding a second component comprising an effective larvacidal amount of a mosquito larva toxin obtained during growth of bacterial cultures, said first and second components giving rise to a synergistic mixture having a greater effectiveness in control of insects than that exhibited by either the first or second component alone.

8. The method of claim 7, wherein the first component forms an insoluble monomolecular layer having a thin layer of oil in the top thereof.

9. A method according to claim 7 or 8 wherein said second component comprises a toxin derived from a bacillus selected from the group consisting of *Bacillus thuringiensis* and *Bacillus sphaericus*.

* * * * *